United States Patent [19]
Ninomiya et al.

[11] Patent Number: 4,762,947
[45] Date of Patent: Aug. 9, 1988

[54] PROCESS FOR PRODUCING 2,2-DIMETHYL-1,3-PROPANEDIOL MONO(HYDROXYPIVALATE)

[75] Inventors: Teruyuki Ninomiya, Okayama; Yumiko Kudo, Kurashiki, both of Japan

[73] Assignee: Mitsubishi Gas Chemical Company, Inc., Tokyo, Japan

[21] Appl. No.: 940,379

[22] Filed: Dec. 11, 1986

[30] Foreign Application Priority Data

Dec. 25, 1985 [JP] Japan ................................ 60-290811

[51] Int. Cl.$^4$ ............................................ C07C 69/675

[52] U.S. Cl. ..................................... 560/189; 502/152

[58] Field of Search .......................... 560/189; 502/152

[56] References Cited

U.S. PATENT DOCUMENTS

| | | | |
|---|---|---|---|
| 3,057,911 | 10/1962 | Firch | 560/189 |
| 3,505,369 | 4/1970 | Deffner | 502/152 |
| 3,641,117 | 2/1972 | Platz et al. | 560/189 |
| 3,729,506 | 4/1973 | Merger et al. | 560/189 |
| 3,862,215 | 1/1975 | Merger et al. | 560/189 |
| 4,617,408 | 10/1986 | Nestler et al. | 502/152 |

FOREIGN PATENT DOCUMENTS

| | | | |
|---|---|---|---|
| 2500311 | 7/1976 | Fed. Rep. of Germany | 560/189 |
| 45-39688 | 12/1970 | Japan . | |
| 46-41888 | 12/1971 | Japan . | |
| 47-18096 | 5/1972 | Japan . | |
| 40-51218 | 5/1974 | Japan . | |
| 51-26414 | 8/1976 | Japan . | |

*Primary Examiner*—Donald B. Moyer
*Assistant Examiner*—Bruce D. Gray
*Attorney, Agent, or Firm*—Armstrong, Nikaido, Marmelstein & Kubovcik

[57] ABSTRACT

This invention relates to a process for producing 2,2-dimethyl-1,3-propanediol mono(hydroxypivalate) which comprises condensing two molecules of hydroxypivaldehyde in the presence of an organometallic complex containing a transition metal and organic ligands selected from the group consisting of acetylacetonato, fluoracetylacetonato and benzoylacetonato.

5 Claims, No Drawings

PROCESS FOR PRODUCING 2,2-DIMETHYL-1,3-PROPANEDIOL MONO(HYDROXYPIVALATE)

BACKGROUND OF THE INVENTION

1. Field of the Invention

The present invention relates to a process for producing 2,2-dimethyl-1,3-propanediol mono(nydroxypivalate).

2,2-Dimethyl-1,3-propanediol mono(hydroxypivalate) 2,2-dimethyl-3-hydroxypropyl-2,2-dimethyl-3-hydroxy propionate (hereinafter, simply referred to as DPHE) is a kind of ester-glycol having a neo structure. Owing to its molecular structure, it is characteristically excellent in heat resistance, weather resistance and hydrolysis resistance. Thus, it is watched with interest mainly as a starting material and modifier of polyesters, polyurethanes and polyacrylates and as a plasticizer or an lubricant.

2. Description of the Prior Art

DPHE is formed by a self-condensation reaction of hydroxypivaldehyde 2,2-dimethyl-3-hydroxypropanol (hereinafter, simply referred to as HPA) as expressed by the following reaction scheme:

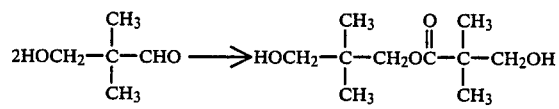

As the prior process for producing DPHE by the self-condensation of HPA, the process mentioned in U.S. Pat. No. 3,057,911 which comprises heating HPA in the absence of catalyst is known.

However, the process which comprises simply heating HPA in the absence of catalyst is industrially impractical because the reaction progresses too slowly and by-products are formed in a large amount.

Thus, as its improvement, a number of processes which comprise carrying out the reaction in the presence of a catalyst have been proposed [for example, the processes using calcium hydroxide, barium hydroxide, strontium hydroxide and the like (Japanese Patent Publication No. 39,688/70, Japanese Patent Kokai (Laid-Open) No. 51,218/74); the processes using manganese catalyst (Japanese Patent Publication No. 41,888/71); the process using tertiary amine formate (Japanese Patent Publication No. 18,096/72); and the process using titanic ester or its polymer (Japanese Patent Publication No. 26,414/76)].

However, the catalysts proposed in the above-mentioned prior patents are disadvantageous in that they are unsatisfactory from the viewpoint of reaction velocity, some of them form a large amount of by-product, and some of them lose their catalyst activity when a slight quantity of water is present in the system. Further, some of these catalysts cause a coloration of reaction product or induce a thermal decomposition to lower the product yield to a great extent.

SUMMARY OF THE INVENTION

With the aim of overcoming these disadvantages of the prior arts, the present inventors have studied various catalysts to find that acetonato complex compounds have a quite excellent catalytic effect. Based on this finding, the present invention has been accomplished.

Thus, the present invention relates to a process for producing 2,2-dimethyl-1,3-propanediol mono(hydroxypivalate) which comprises subjecting HPA to a condensation reaction in the presence of an acetonato complex catalyst.

The HPA used as the starting material in the invention can easily be obtained by reacting isobutyraldehyde with formaldehyde in the presence of a basic catalyst.

The process of the invention is carried out by adding a desired quantity of catalyst, i.e. an acetonato complex compound, to HPA and heating the mixture to make progress the self-condensation of HPA.

In the invention, the reaction temperature is usually 60° C. to 180° C. and preferably 90° C. to 150° C. The reaction progresses relatively speedily. Thus, at the above-mentioned temperature, it is completed generally in 5 to 90 minutes and usually 10 to 60 minutes. In the invention, accordingly, the reaction time is a period from the addition of the catalyst to the stopping of the reaction.

The acetonato complex compounds used in the invention as a catalyst are compounds of transition metals belonging to Group III to Group VIII of the periodic table (IUPAC version, Groups 3–17 of the ACS periodic table), such as acetylacetonato complex compounds, fluoroacetylacetonato complex compounds, benzoylacetylacetonato complex compounds and the like. Examples of said acetylacetonato complex compound include trisacetylacetonato-aluminum [Al(CH$_2$COCH$_2$COCH$_3$)$_3$], tris-acetylacetonato chromium (III) [Cr(CH$_2$COCH$_2$COCH$_3$)$_3$], tris-acetylacetonato-indium [In(CH$_2$COCH$_2$COCH$_3$)$_3$], bis-acetylacetonato-lead [Pb(CH$_2$COCH$_2$COCH$_3$)$_2$], bis-acetylacetonato-manganese [Mn(CH$_2$COCH$_2$COCH$_3$)$_2$], tris-acetylacetonato-manganese [Mn(CH$_2$COCH$_2$COCH$_3$)$_3$], tris-acetylacetonato-iron [Fe(CH$_2$COCH$_2$COCH$_3$)$_3$], bis-acetylacetonato-molybdenum (IV) dioxide [MoO$_2$(CH$_2$COCH$_2$COCH$_3$)$_2$], bis-acetylacetonato-nickel [Ni(CH$_2$COCH$_2$COCH$_3$)$_2$, bis-acetylacetonato-palladium (II) [Pd(CH$_2$COCH$_2$COCH$_3$)$_2$], tris-acetylacetonato-vanadium [V(CH$_2$COCH$_2$COCH$_3$)$_3$], bis-acetylacetonato-vanadium oxide [VO(CH$_2$COCH$_2$COCH$_3$)$_2$], tetrakis-acetylacetonato-zirconium [Zr(CH$_2$COCH$_2$COCH$_3$)$_4$], tetrakis-acetylacetonato-yttrium [Y(CH$_2$COCH$_2$COCH$_3$)$_4$], tetrakis-acetylacetonato-thorium [Th(CH$_2$COCH$_2$COCH$_3$)$_4$], tetrakis-acetylacetonato-hafnium [Hf(CH$_2$COCH$_2$COCH$_3$)$_4$], bis-acetylacetonato-uranium (IV) oxide [UO$_2$(CH$_2$COCH$_2$COCH$_3$)$_2$], tetrakis-acetylacetonato-uranium [U(CH$_2$COCH$_2$COCH$_3$)$_2$], bis-acetylacetonato-titanium butoxide [Ti(OC$_4$H$_9$)$_2$(CH$_2$COCH$_2$COCH$_3$)$_2$], bis-acetylacetonato-titanium (IV) oxide [TiO(CH$_2$COCH$_2$COCH$_3$)$_2$] and the like.

Examples of said fluoroacetylacetonato complex compound include tris-fluroacetylacetonate-indium [In(CH$_2$COCH$_2$COCF$_3$)$_3$], tris-fluoroacetylacetanato-lead [Pb(CH$_2$COCH$_2$COCF$_3$)$_3$], tetrakis-trifluoroacetylacetonato-thorium [Th(CH$_2$COCH$_2$COCF$_3$)$_4$], tetrakis-trifluoroacetylacetonato-zirconium [Zr(CH$_2$COCH$_2$COCF$_3$)$_4$], trifluoroacetylacetoantopalladium [Pd(CH$_2$COCH$_2$COCF$_3$)$_2$], and the like. Examples of said benzoylacetylacetonato complex compound include tris-benzoylacetonato-aluminum [Al(C$_6$H$_5$COCH$_2$COCH$_3$)$_3$]. Among these compounds, bis-acetylacetonato-manganese, tris-acetylacetonato-manganese, tris-acetylacetonato-titanium oxide, tris-acetylacetonato-iron, bis-acetylacetonato-nickel, trisacetylacetonato-vanadium, bis-acetylacetonato-vanadium oxide, tetrakis-acetylacetonato-zirconium, tetrakis-trifluoroacetylacetonato-zirconium, trifluoroacetylacetonato-palladium and the like are more preferable from the viewpoint of availability and handling. As the catalyst used in the invention, those soluble into the reaction system are particularly preferred.

The catalyst of the invention mentioned above is used usually in an amount of 0.005 to 0.5% by weight and preferably in an amount of 0.01 to 0.1% by weight, based on the weight of starting HPA. In the invention, these catalysts are put to use in the form of solid itself or liquid itself. If desired, however, the catalysts are put to use after dissolving or suspending them into an appropriate solvent inert to the reaction, for example a hydrocarbon such benzene, toluene, xylene and the like. In the invention, the catalyst is added to HPA either directly or after fusing HPA. Many of the above-mentioned catalysts used in the invention are non-hydrolyzable so that they do not lose their catalyst activity even if contacted with a minute quantity of water. Accordingly, the catalyst may also be added to the starting material containing a small quantity of water.

After the reaction, the catalyst is separated from the reaction product. Since the product can be somewhat colored in some cases, this separation of catalyst may be carried out for the purpose of simultaneously purifying the product. This separation and purification can be performed by a distillation. The intended product is obtained in the form of distillate.

The process of the invention may be carried out by batch method, semi-batch method or continuous method, too.

According to the present invention, a DPHE of high purity can be obtained in a short period of time, in a high yield, and with an as possible lessened formation of by-products. Further, since the catalyst of the invention is excellent in heat stability and hydrolysis resistance, it can easily be separated from the intended product, i.e. DPHE, and the recovered catalyst can be reused.

DESCRIPTION OF THE PREFERRED EMBODIMENTS

Next, examples of the invention will be shown below. The comparative examples refer to the cases using prior catalysts. In the examples, "%" and "parts" mean "% by weight" and "parts by weight", respectively.

EXAMPLE 1

In a 500 ml four-necked round bottom flask equipped with a condenser, a thermometer, a nitrogen gas inlet nozzle and a stirrer, 300 parts of powdery HPA having a purity of 99.8% was heated and melted. When the temperature had reached 90° C., 0.03%, based on HPA, of tetrakis-acetylacetonato-zirconium Zr(CH$_2$COCH$_2$COCH$_3$)$_4$] was added as a catalyst. Simultaneously with the addition of the catalyst, the heating was stopped and the mixture was allowed to cool. The temperature once ascended to 148° C. in 5 minutes and subsequently descended slowly. When the temperature had reached 130° C., the mixture was rapidly cooled to stop the reaction. The period of time from the addition of the catalyst to stopping of the reaction was 25 minutes.

Analyses revealed that the product thus obtained had the following composition:

| | |
|---|---|
| HPA | 0.05% |
| 2,2-Dimethyl-1,3-propanediol | 0.25% |
| 2,2-Dimethyl-1,3-propanediol mono(isobutyrate) | 0.11% |
| DPHE | 99.30% |
| Unknown components | 0.29% |

Although the above-mentioned composition was satisfactory as that of an industrial product, it had a light yellow color and it contained the catalyst. Accordingly, it was subjected to distillation under reduced pressure. As the result, 288 parts of DPHE was obtained as a main distillate boiling at 140°–153° C./3–6 mm Hg.

Analyses revealed that this main distillate DPHE had a melting point of 48.4° C., a hydroxyl value of 539.6 and a molten color (APHA) of 10 or below.

EXAMPLE 2

The procedure of Example 1 was repeated with the same apparatus and starting material HPA as in Example 1, except that 0.03% of tris-acetylacetonato-vanadium [V(CH$_2$COCH$_2$COCH$_3$)$_3$] was used as catalyst. When temperature had reached 130° C., the catalyst was added. After addition of the catalyst, the temperature ascended to 155° C. in 5 minutes. After maintaining this temperature for 30 minutes, the reaction mixture was allowed to cool. When the temperature had reached 130° C., the mixture was rapidly cooled to stop the reaction. The period of time from the addition of the catalyst to the stopping of reaction was 40 minutes.

Analyses of the product thus obtained were as follows:

| | |
|---|---|
| HPA | 2.65% |
| 2,2-Dimethyl-1,3-propanediol | 0.95% |
| 2,2-Dimethyl-1,3-propanediol mono(isobutyrate) | 0.01% |
| DPHE | 96.25% |
| Unknown components | 0.14% |

This product was subjected to a distillation under reduced pressure in the same manner as in Example 1 to obtain 274 parts of DPHE as a main distillate boiling at 140°–153° C./3–6 mm Hg. Analyses revealed that this main distillate DPHE had a melting point of 49.2° C., a hydroxyl value of 541.0, and a molten color (APHA) of 10 or below.

EXAMPLE 3

The procedure of Example 1 was repeated with the same apparatus and starting HPA as in Example 1, except that 0.03% of tetrakis-trifluoroacetylacetonato-zirconium [Zr(CH$_2$COCH$_2$COCF$_3$)$_4$] was used as catalyst and the reaction time was 30 minutes.

Analyses of the product were as follows:

| | |
|---|---|
| HPA | 3.50% |
| 2,2-Dimethyl-1,3-propanediol | 0.20% |
| 2,2-Dimethyl-1,3-propanediol mono(isobutyrate) | 0.05% |
| DPHE | 95.10% |
| Unknown components | 1.15% |

This product was subjected to a distillation under reduced pressure in the same manner as in Example 1 to obtain 280 parts of DPHE as a main distillate boiling at 140°-153° C./3-6 mm Hg. Analyses of this main distillate DPHE revealed that it had a melting point of 49.0° C., a hydroxyl value of 542.2 and a molten color (APHA) of 10 or below.

EXAMPLE 4

The procedure of Example 1 was repeated, except that 0.03% of acetylacetonato-titanium oxide [TiO(CH$_2$COCH$_2$COCH$_3$)$_2$] was used as catalyst and the reaction time was 60 minutes.

Analyses of the product were as follows:

| HPA | 0.50% |
|---|---|
| 2,2-Dimethyl-1,3-pronanediol | 0.10% |
| 2,2-Dimethyl-1,3-propanediol mono(isobutyrate) | 0.00% |
| DPHE | 99.00% |
| Unknown components | 0.40% |

This product was subjected to a distillation under reduced pressure in the same manner as in Example 1 to obtain 286 parts of DPHE as a main distillate boiling at 140°-153° C./3-6 mm Hg. Analyses revealed that this DPHE had a melting point of 49.0° C., a hydroxyl value of 540.5 and a molten color (APHA) of 10 or below.

EXAMPLE 5

The procedure of Example 1 was repeated with the same apparatus and starting HPA as in Example 1, except that 0.05% of tris-acetylacetonato-iron (III) [Fe(CH$_2$COCH$_2$COCH$_3$)$_3$] was used as catalyst and the reaction time was 90 minutes.

Analyses of the product were as follows:

| HPA | 1.6% |
|---|---|
| 2,2-Dimethyl-1,3-propanediol | 0.3% |
| 2,2-Dimethyl-1,3-propanediol mono(isobutyrate) | 0.09% |
| DPHE | 97.4% |
| Unknown components | 0.6% |

This product was subjected to a distillation under reduced pressure in the same manner as in Example 1 to obtain 285 parts of a main distillate boiling at 140°-153° C./3-6 mm Hg. Analyses revealed that this DPHE had a melting point of 48.5° C., a hydroxyl value of 544.5 and a molten color (APHA) of 10 or below.

EXAMPLE 6

The procedure of Example 1 was repeated with the same apparatus and starting HPA as in Example 1, except that 0.05% of acetylacetonato-vanadium oxide [VO(CH$_2$COCH$_2$COCH$_3$)$_2$] was used as catalyst and the reaction time was 45 minutes.

Analyses of the product were as follows:

| HPA | 2.4% |
|---|---|
| 2,2-Dimethyl-1,3-propanediol | 0.8% |
| 2,2-Dimethyl-1,3-propanediol mono(isobutyrate) | 0.2% |
| DPHE | 96.3% |
| Unknown components | 0.3% |

This product was subjected to a distillation under reduced pressure in the same manner as in Example 1 to obtain 278 parts of a main distillate boiling at 140°-153° C./3-6 mm Hg. Analyses revealed that this main distillate DPHE had a melting point of 48.0° C., a hydroxyl value of 545 and a molten color (APHA) of 10 or below.

EXAMPLE 7

The procedure of Example 1 was repeated with the same apparatus and starting HPA as in Example 1, except that 0.1% of tris-acetylacetonato-manganese [Mn(CH$_2$COCH$_2$COCH$_3$)$_3$] was used as catalyst and the reaction time was 60 minutes.

Analyses of the product were as follows:

| HPA | 3.2% |
|---|---|
| 2,2-Dimethyl-1,3-propanediol | 0.1% |
| 2,2-Dimethyl-1,3-propanediol mono(isobutyrate) | 0.02% |
| DPHE | 96.1% |
| Unknown components | 0.58% |

This product was subjected to a distillation under reduced pressure in the same manner as in Example 1 to obtain 283 parts of a main distillate boiling at 140°-153° C./3-6 mm Hg. Analyses revealed that this main distillate DPHE had a melting point of 48.5° C., a hydroxyl value of 548 and a molten color (APHA) of 10 or below.

COMPARATIVE EXAMPLE 1

The procedure of Example 1 was repeated, except that 0.06% of tetraisopropyl titanate was used as catalyst and the reaction time was 30 minutes.

Analyses of the product were as follows:

| HPA | 7.1% |
|---|---|
| 2,2-Dimethyl-1,3-propanediol | 2.4% |
| 2,2-Dimethyl-1,3-propanediol mono(isobutyrate) | 0.5% |
| DPHE | 87.2% |
| Unknown components | 2.8% |

This product was subjected to a distillation under reduced pressure in the same manner as in Example 1 to obtain 250 parts of DPHE as a main distillate boiling at 140°-153° C./3-6 mm Hg. Analyses revealed that this main distillate DPHE had a melting point of 48.0° C., a hydroxyl value of 533 and a molten color (APHA) of 30.

COMPARATIVE EXAMPLES 2-7

The procedure of Example 1 was repeated with the same reactor and starting HPA. The kind and amount of catalyst, the reaction temperature and the reaction time were as shown in Table 1.

Analyses of the products thus obtained were as shown in Table 1.

TABLE 1

| | | 2 | 3 | 4 | 5 | 6 | 7 |
|---|---|---|---|---|---|---|---|
| Reaction conditions | Catalyst | None | Ca(OH)$_2$ | KMnO$_4$ | Tetrabutyl titanate | Triethylamine formate | Li(OH)$_2$ |

TABLE 1-continued

|  |  | 2 | 3 | 4 | 5 | 6 | 7 |
|---|---|---|---|---|---|---|---|
|  | Amount, % by wt. | — | 3.0 | 0.25 | 0.2 | 0.3 | 10.0 |
|  | Reaction temperature, °C. | 130 | 130 | 130 | 130 | 130 | 130 |
|  | Reaction time, min. | 180 | 360 | 180 | 30 | 120 | 60 |
| Composition of reaction mixture % | HPA | 31.5 | 18.1 | 8.5 | 8.6 | 16.5 | 5.8 |
|  | 2,2-Dimethyl-1,3-propanediol | 5.2 | 4.3 | 2.8 | 1.1 | 3.3 | 1.9 |
|  | 2,2-dimethyl-1,3-propanediol mono-(isobutyrate) | 1.4 | 2.5 | 3.7 | 0.8 | 4.0 | 2.5 |
|  | DPHE | 58.5 | 72.5 | 84.6 | 86.7 | 67.5 | 88.9 |
|  | Unknown components | 3.4 | 2.6 | 0.4 | 2.8 | 8.7 | 0.9 |

Note
In the cases of Ca(OH)$_2$, KMnO$_4$ and Li(OH)$_2$ catalysts, decomposition of DPHE took place when the reaction mixture was distilled.
In the cases of tetrabutyl titinate and triethylamine formate catalysts, the catalyst contaminated the reaction product to color the latter remarkably.

What is claimed is:

1. A process for producing 2,2-dimethyl-3-hydroxypropyl-2,2-dimethyl-3-hydroxypropionate which comprises condensing two molecules of 2,2-dimethyl-3-hydroxypropanal in the presence of an organometallic complex compound containing a transition metal selected from the group consisting of Group III A, Group III B, Group IV A, Group IV B, Group V B, Group VI B, Group VII B, Group VIII and the Actinide series of the Periodic Table and having ligands selected from the group consisting of acetylacetonato, fluoroacetylacetonato and benzoylacetonato.

2. A process according to claim 1, wherein said transition metal is one member selected from the group consisting of Ti, Zr, V, Mn, Fe, Co, Ni, and Pd.

3. A process according to claim 1, wherein said organometallic complex compound is an acetylacetonato complex compound selected from the group consisting of bis-acetylacetonato-manganese, tris-acetylacetonato-manganese, tris-acetylacetonato-iron, bis-acetylacetonato-nickel, tris-acetylacetonato-vanadium, bis-acetylacetonato-vanadium oxide, tetrakis-acetylacetonato-zirconium and bis-acetylacetonato-titanium oxide.

4. A process according to claim 1, wherein said organometallic complex compound is a fluoroacetylacetonato complex compound selected from the group consisting of tetrakis-trifluoroacetylacetonato-zirconium and trifluoroacetylacetonato-palladium.

5. A process according to claim 1, wherein said organometallic complex compound is used in an amount of 0.005 to 0.5% by weight based on the weight of the starting 2,2-dimethyl-3,3-hydroxpropanal.

* * * * *